United States Patent
Pozzi

[11] Patent Number: 6,062,854
[45] Date of Patent: May 16, 2000

[54] APPARATUS HAVING SCREW MEANS FOR THE MANDIBULAR DISTRACTION

[75] Inventor: Alessandro Pozzi, Florence, Italy

[73] Assignee: Leone S.p.A., Italy

[21] Appl. No.: 09/037,845

[22] Filed: Mar. 10, 1998

[30] Foreign Application Priority Data

May 29, 1997 [IT] Italy ................................. FI97A0127

[51] Int. Cl.$^7$ .................................................. A61C 3/00
[52] U.S. Cl. .................................................. 433/7; 433/18
[58] Field of Search .......................................... 433/7, 18

[56] References Cited

U.S. PATENT DOCUMENTS

| | | | |
|---|---|---|---|
| 3,800,420 | 4/1974 | Quaknine | 433/7 |
| 4,347,054 | 8/1982 | Kraus et al. | 433/7 |
| 4,482,318 | 11/1984 | Förster | 433/7 |
| 5,328,364 | 7/1994 | Doyle | 433/18 |
| 5,599,183 | 2/1997 | Razdolsky et al. | 433/53 |

FOREIGN PATENT DOCUMENTS

| | | | |
|---|---|---|---|
| 998076 | 1/1952 | France | 433/7 |
| 980322 | 1/1965 | United Kingdom | 433/7 |
| WO 94/10933 | 5/1994 | WIPO . | |

OTHER PUBLICATIONS

LEONE S.P.A., Rapid Exapander—For Palatal Suture Separation, Leone catalogue.

*Primary Examiner*—John J. Wilson
*Attorney, Agent, or Firm*—McGlew and Tuttle, P.C.

[57] ABSTRACT

Apparatus having screw means for the mandibular distraction comprising, for each side of the dental arch under treatment, at least two bands (1, 10) capable of being fitted on predetermined dental elements and fixed to corresponding bodies (5, 6) with two parallel guide rods (7) going therethrough and disposed on opposite sides with respect to the expansion screw (2) which drives said bodies (5, 6) away from each other to allow for the corresponding stretching apart of said bands (1, 10), said screw (2) being provided with a driving portion (20) for driving it into rotation under the operator's control to cause the said separation of the orthodontic bands (1, 10) associated to the bodies (5, 6). The driving portion (20) of the screw (2) is arranged, in correspondence of the head of the screw (2), parallel to said rods (7): the driving portion (20) of the screw (2) facing the mouth of the patient to be engagable by a driving tool (8).

4 Claims, 4 Drawing Sheets

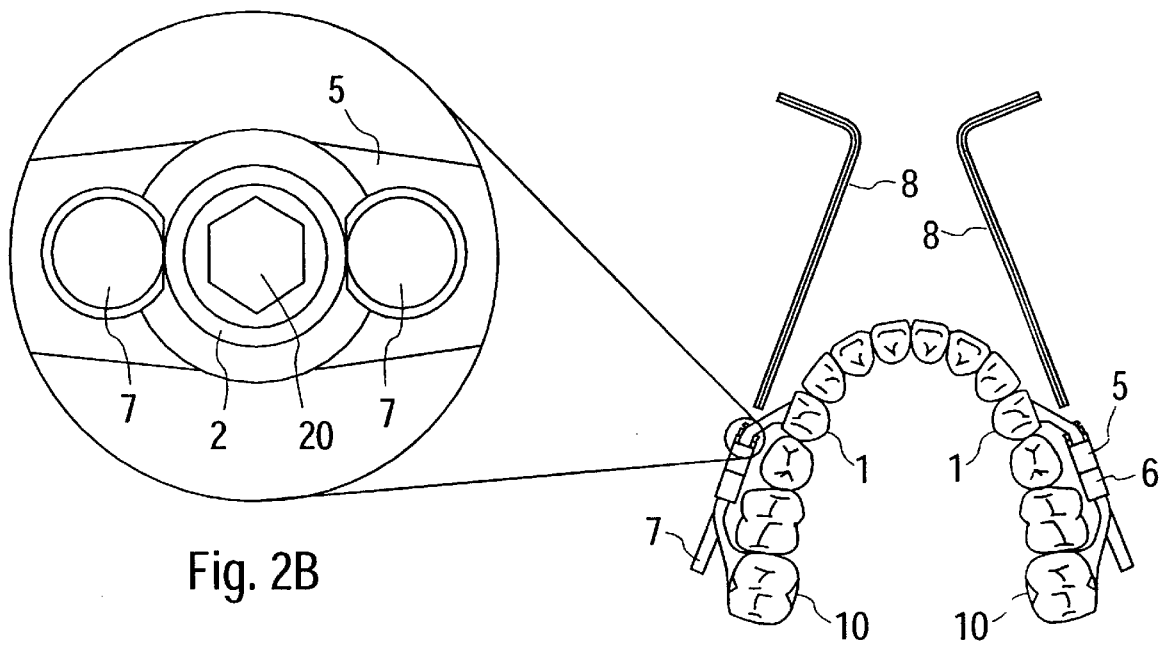
Fig. 2B
Fig. 2A
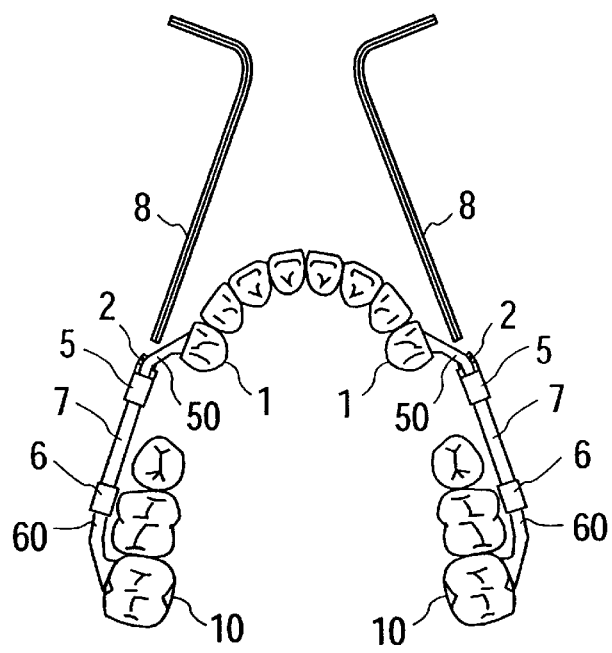
Fig. 2C

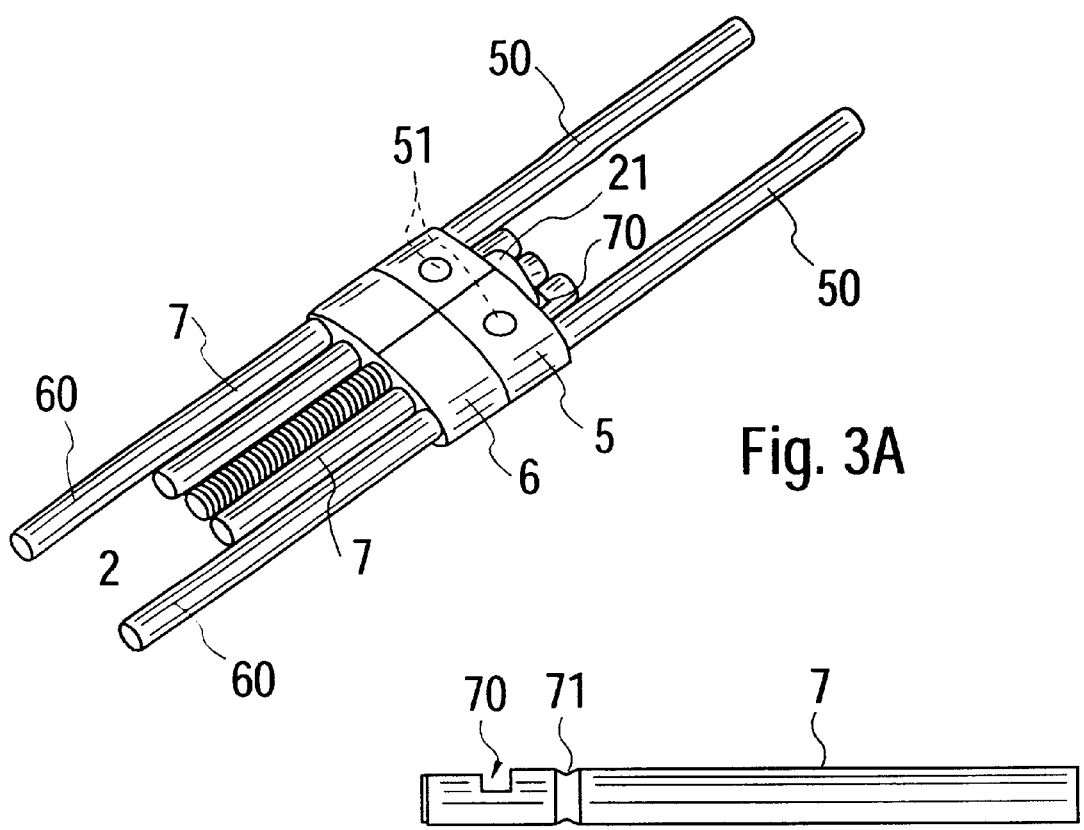
Fig. 3A
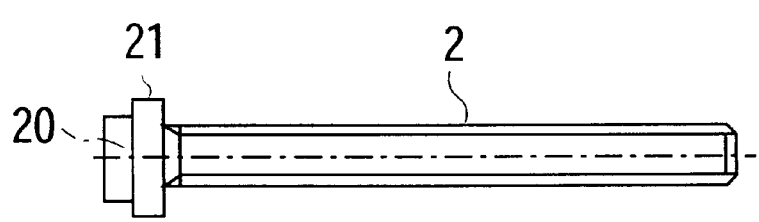
Fig. 3B
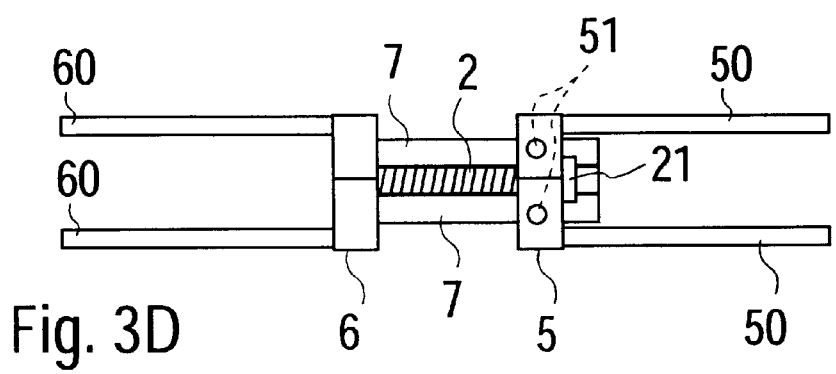
Fig. 3C
Fig. 3D

6,062,854

APPARATUS HAVING SCREW MEANS FOR THE MANDIBULAR DISTRACTION

FIELD OF THE INVENTION

The present invention refers to an apparatus having screw means for the mandibular distraction.

BACKGROUND OF THE INVENTION

It is known, in case of transverse deficiency of superior maxilla, to resort to a corrective expansion therapy implemented by applying a fast expansion force of high intensity so as to cause the expansion with fracture and subsequent osteogenesis of the maxillary bone. To obtain this result use can be made, for example, of screw devices such as the one disclosed in U.S. Pat. Nos. 4,347,054 and 4,482,318, as well as WO 94/10933, and of the screw model A0620 manufactured by the same Applicant. In case of an expansion in anteroposterior direction concerning both the maxillary and mandibular bones, where no bone sutures to be expanded nor fractures are present, an operating technique of distraction and osteogenesis is applied which uses screws such as the one described in the U.S. Pat. No. 5,599,183 which refers to an apparatus for assembling a device for mandibular distraction. This type of device comprises, essentially, a plurality of orthodontic bands allowing it to be fixed to predetermined dental elements of both sides of the concerned dental arch, which bands are engaged to expansion screws located externally and sideway thereof so as to be moved away from each other by an expansion operated by rotating a screw-actuating portion by means of pin element to be inserted into holes or cavities suitably provided on a plane orthogonal to the longitudinal axis of each screw. In this way, there is obtained the distraction of the anterior portion from, for example, the posterior one.

Illustrated in FIG. 1 of the attached drawings is an apparatus of the type mentioned above, wherein (1, 10) indicate the orthodontic bands, (2) is the expansion screws, (3) refers to the acting portion of the same screws and (4) indicates the means for operating the distraction.

However, experience has shown that the operation of the screws of the type above described is very difficult to carry out owing to the small space available between the screws and the inner surface of the corresponding cheeks, and to the consequent reduced visibility for the operator who has to drive the screws.

SUMMARY AND OBJECTS OF THE INVENTION

The main object of the present invention is to overcome the said drawback.

This result has been achieved, according to the invention, by providing an apparatus having the screw means for the mandibular distraction. Each side of the dental arch under treatment has at least two bands capable of being fitted on predetermined dental elements and fixed to corresponding bodies with two parallel guide rods going therethrough and disposed on opposite sides with respect to expansion screw. The expansion screws drive the bodies away from each other to allow for the corresponding stretching apart of the bands. The screw are provided with a driving portion for driving it into rotation under the operator's control to cause the separation of the orthodontic bands associated to the bodies. The driving portion of the screw is arranged, in correspondence of the head of the screw, parallel to said rods. The driving portion of the screw facing the mouth of the patient is engagable by a driving tool.

The advantages deriving from the present invention lie essentially in that it is possible to facilitate the expansion of the screw by making the expansion operation easier, safer, more accurate and rapid; that an expansion screw according to the invention is simple to make, cost-effective and reliable even after a prolonged service life. These and other advantages and characteristics of the invention will be best understood by anyone skilled in the art from a reading of the following description in conjunction with the attached drawings given as a practical exemplification of the invention, but not to be considered in a limitative sense, wherein:

BRIEF DESCRIPTION OF THE DRAWINGS

FIG. 2A is a plan view of an apparatus with expansion screw for orthodontic use according to the invention, wherein the orthodontic bands exhibit no stretching apart;

FIG. 2B shows an enlarged detail of the apparatus of FIG. 2A;

FIG. 2C shows the apparatus of FIG. 2A in which the orthodontic bands are stretched apart to their maximum extent;

FIG. 3A is a perspective view of the expansion assembly in an apparatus according to a first embodiment of the invention;

FIG. 3B shows in detail a guide means for the assembly of FIG. 3A;

FIG. 3C shows in detail the screw of the assembly of FIG. 3A;

FIG. 3D is a side view of the assembly of FIG. 3A in a condition of maximum extension;

DESCRIPTION OF THE PREFERRED EMBODIMENT

Figure 1:
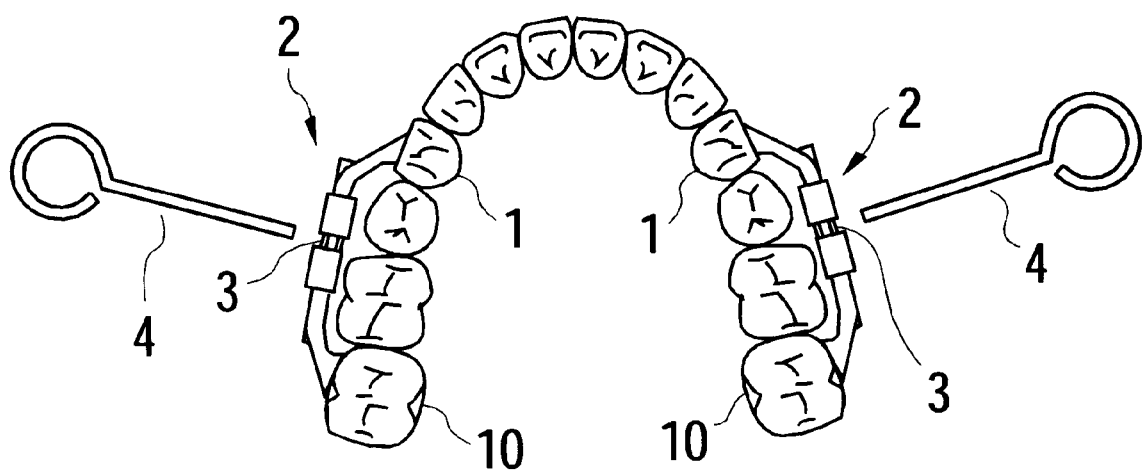
FIG. 1 is a plan view of an apparatus with expansion screw for orthodontic use of known type.

Reduced to its basic structure, and reference being made to the figures of the attached drawings, wherein like or corresponding elements have been designated by the same reference number, an orthodontic retractor according to the invention comprises, for each side of the dental arch under treatment, at least two bands (1, 10) capable of being fitted on predetermined dental elements, for example an anterior band (1) for the first premolar and posterior band (10) for the second molar, fixed to corresponding bodies (5, 6) with two parallel guide rods (7) going therethrough and disposed on opposite sides with respect to the expansion screw (2) which drives said bodies (5, 6) away from each other to allow for the corresponding stretching apart of said bands (1, 10); said screw (2) being provided with means for the rotation thereof under the control of the operator.

Figure 4A:
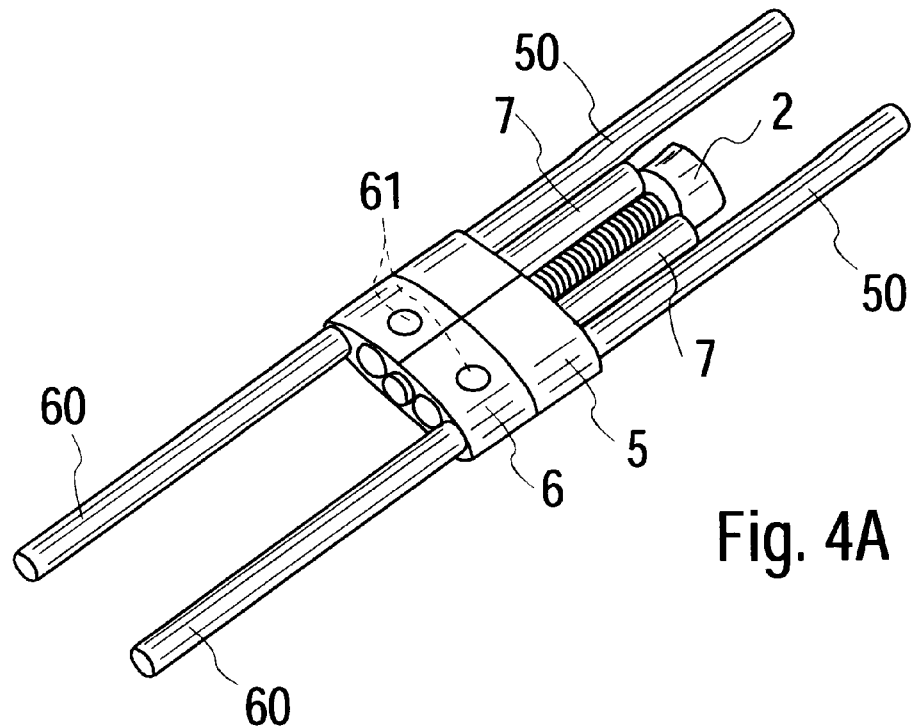
FIG. 4A is a perspective view of the expansion assembly in an apparatus according to a further embodiment of the invention.

As shown in FIGS. 2A and 2C, the body (5) is associated to the anterior band (1) and the body (6) to the posterior band (10). In FIGS. 3A, 3D, 4A and 4D the bands (1, 10) are omitted, the figures showing only the extensions (50, 60) of bodies (5, 6) to which the same bands are fixed. As shown in FIGS. 2A–2C, said rods are arranged, along the vestibular side of the mandibular arch, parallel to the axis which virtually join the centers of the bands (1, 10).

Advantageously, according to the invention, said means for driving the screw (2) consist of a cavity (20) of predetermined shape, located in correspondence of the head of the same screw (2) and to be engaged by a driving tool (8) whose cross-section has a shape corresponding to that of the said cavity (20): the head of the screw (2) facing the mouth of the patient, so as to facilitate the intraoral activation of the apparatus, with no hindrance to the operator. The longitudinal axis of said cavity (20) is parallel to the rods (7).

As illustrated in FIGS. 2A and 2C of the attached drawings, upon activation of the apparatus, the tool (8) can be used to drive the screw (2) with no contact with the cheeks of the patient who, in this way, undergoes the intervention without further discomfort. Moreover, the screw cavity (20) intended to receive the tool (8) is far more visible to the operator than in case of the traditional screws that can be driven only laterally, and not frontally as provided by the present invention.

The cavity (20) provided in the head of said screw (2) may have any suitable shape. Preferably, the cross-section shape of the cavity (20) is polygonal, as illustrated in FIG. 2B, to allow Allen wrenches to be used as driving tools.

According to the embodiment shown in FIGS. 3A–3D of the drawings, of said bodies (5, 6) the anterior one (5) exhibits, when assembled for use and disposed on the mouth side, a central longitudinal through hole with a thread corresponding to that of the screw (2), while the other (6) is only drilled to receive the stem of the screw (2), the head of the latter exhibiting a crown (21), for example of circular shape, to be engaged into a corresponding cavity (70) of the two side guides (7). In this way, by rotating, that is, unscrewing the screw (2) by means of the wrench (8) inserted into the cavity (20), there is obtained the separation of the bodies (5, 6) over the whole travel allowed by the guides (7), as shown in FIG. 3D, and thus the correspondent moving away or stretching apart of the orthodontic bands fixed to the elements (50) and (60). Provided in the body (5) are appendixes (51) to be engaged into corresponding grooves (71) of the guides (71) to act as stop means.

Figure 4B:
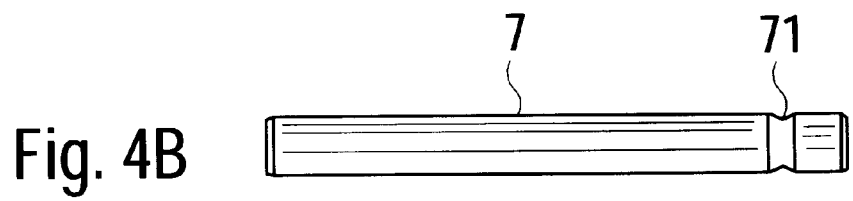
FIG. 4B shows in detail a guide rod for the assembly of FIG. 4A.
Figure 4C:
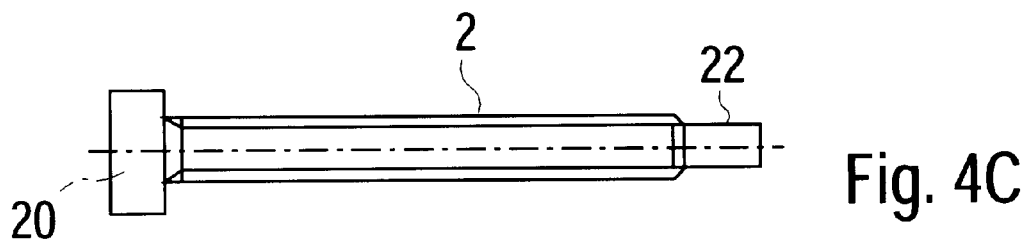
FIG. 4C shows in detail the screw of the assembly of FIG. 4A.
Figure 4D:
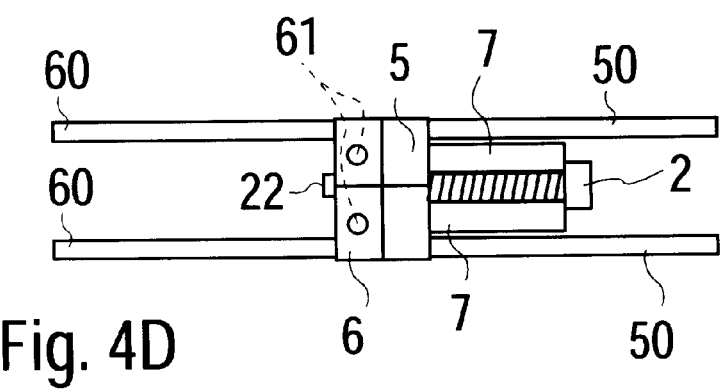
FIG. 4D is a side view of the assembly of FIG. 4A.

According to the embodiment illustrated in FIGS. 4A–4D, of said two bodies (5, 6) associated to the screw (2), the one (5) on the side of the patient's mouth has a central longitudinal through hole with a thread corresponding to that of the screw (2), while the other (6) has a corresponding through hole unthreaded and with an end neck intended to receive a longitudinal end appendix (22) of the screw (2) having a diameter smaller than that of the threaded stem. In this way, the separation of the bodies (5, 6) over the whole travel allowed by the guides (7) is achieved by turning the screw (2) by means of the wrench (8) in the screwing direction. Provided in the body (6) are appendixes (61) intended to engage grooves (71) in the guides (7).

Practically, all the construction details may vary in any equivalent way as far as the shape, dimensions, elements disposition, nature of the used materials are concerned, without nevertheless departing from the scope of the adopted solution idea and, thereby, remaining within the limits of the protection granted to the present patent for industrial invention.

I claim:

1. An apparatus for mandibular distraction, the apparatus comprising:

two orthodontic bands fit on predetermined dental elements in an installed position;

a mouth opening side body connected to one of said two orthodontic bands;

a mouth rear side body connected to another of said two orthodontic bands; a first guide rod going through said mouth opening side body;

a second guide rod going through said mouth rear side body, said first guide rod extending substantially parallel to said second guide rod;

an expansion screw associated with said mouth opening side body and said mouth rear side body for driving said bodies away from each other to allow for the corresponding stretching apart of said two orthodontic bands, said first guide rod and said second guide rod being disposed on opposite sides with respect to said expansion screw, said expansion screw being provided with a driving portion for driving it into rotation under an operator's control to cause said separation of the orthodontic bands associated to the bodies, said driving portion being arranged as a head of said expansion screw and parallel to said rods, said driving portion having a tool engageable side at a mouth opening side of the apparatus to define a tool reception path that is directed at the mouth opening of the patient and not at cheeks of the patient, said tool reception path being formed by an accessible region of said driving portion with no structure of the apparatus disposed in front of said tool engageable side of said driving portion at said mouth opening side of the apparatus whereby said driving portion is engaged by said tool on said mouth opening side of the apparatus and the driving portion is driven into rotation by said tool with said tool remaining on said mouth opening side of said apparatus as the orthodontic bands are caused to seperate.

2. The apparatus according to claim 1, wherein said driving portion of said expansion screw has a cavity of polygonal shape provided in the head of said expansion screw, said cavity defining said tool engaging side.

3. The apparatus according to claim 1, wherein one of said first body and said second body is an anterior body disposed on said mouth side when assembled for use and has a central longitudinal through hole with a thread corresponding to a thread of said expansion screw, and another of said first body and said second body has a bore to receive a stem of said expansion screw, the head of said another of said first body and said second body having a crown to be engaged into a corresponding cavity of said guides.

4. The apparatus according to claim 1, wherein one of said first body and said second body is on the side of the patient's mouth and has a central longitudinal through hole with a thread corresponding to a thread of said screw, while another of said first body and said second body has a corresponding unthreaded through hole with an end neck intended to receive a longitudinal end appendix of the screw and having a diameter smaller than that of the threaded stem.

* * * * *